United States Patent
von Oepen et al.

(10) Patent No.: US 8,052,637 B2
(45) Date of Patent: Nov. 8, 2011

(54) MEDICAL DEVICE BALLOON

(75) Inventors: Randolf von Oepen, Los Altos Hills, CA (US); Travis Yribarren, San Mateo, CA (US)

(73) Assignee: Abbott Laboratories, Redwood City, CA (US)

( * ) Notice: Subject to any disclaimer, the term of this patent is extended or adjusted under 35 U.S.C. 154(b) by 464 days.

(21) Appl. No.: 11/456,487

(22) Filed: Jul. 10, 2006

(65) Prior Publication Data

US 2007/0021772 A1    Jan. 25, 2007

Related U.S. Application Data

(60) Provisional application No. 60/698,581, filed on Jul. 12, 2005.

(51) Int. Cl.
*A61M 29/00* (2006.01)

(52) U.S. Cl. .................. 604/96.01; 604/103.06

(58) Field of Classification Search ............. None
See application file for complete search history.

(56) References Cited

U.S. PATENT DOCUMENTS

| | | | | |
|---|---|---|---|---|
| 5,516,565 A | * | 5/1996 | Matsumoto | 428/35.7 |
| 5,700,243 A | * | 12/1997 | Narciso, Jr. | 604/102.01 |
| 5,718,861 A | | 2/1998 | Andrews et al. | |
| 5,728,063 A | * | 3/1998 | Preissman et al. | 604/103.09 |
| 6,488,688 B2 | * | 12/2002 | Lim et al. | 606/108 |
| 6,620,127 B2 | * | 9/2003 | Lee et al. | 604/96.01 |
| 2003/0028211 A1 | * | 2/2003 | Crocker et al. | 606/192 |
| 2005/0214339 A1 | * | 9/2005 | Tang et al. | 424/423 |

FOREIGN PATENT DOCUMENTS

| | | |
|---|---|---|
| EP | 560984 | 9/1993 |
| EP | 628586 | 12/1994 |
| WO | WO 2005/056078 | 6/2005 |
| WO | WO 2005/118045 | 12/2005 |
| WO | WO 2007/008784 | 1/2007 |

OTHER PUBLICATIONS

European Search Report for appl. 06786762.2, mailed Jul. 17, 2009, 5 pgs.

* cited by examiner

*Primary Examiner* — Christopher D Koharski

(74) *Attorney, Agent, or Firm* — Randy Shen, J.D.

(57) ABSTRACT

The present invention relates to medical devices that can be placed in bodily conduits. The invention particularly relates to balloons and catheters using such balloons for administering treatments to widen constricted passages, deliver therapeutic agents, deliver endoprosthesis' or perform other medical procedures. The balloon catheter can include an expandable balloon disposed adjacent a distal end of an elongated catheter shaft. The balloon can be constructed of a novel absorbable biomaterial.

6 Claims, 3 Drawing Sheets

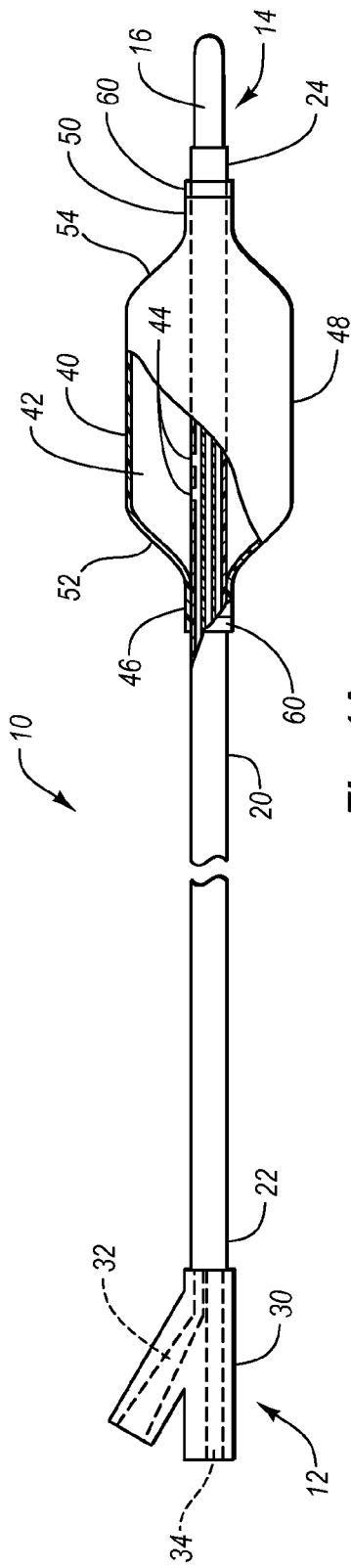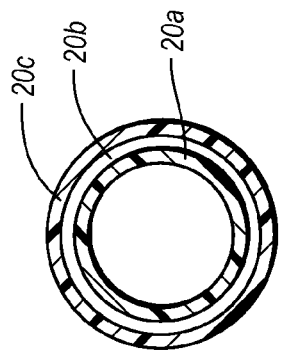

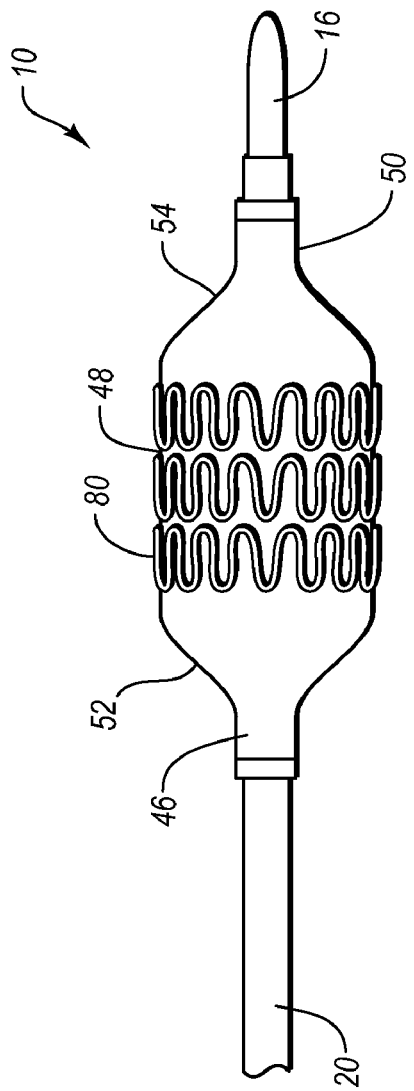
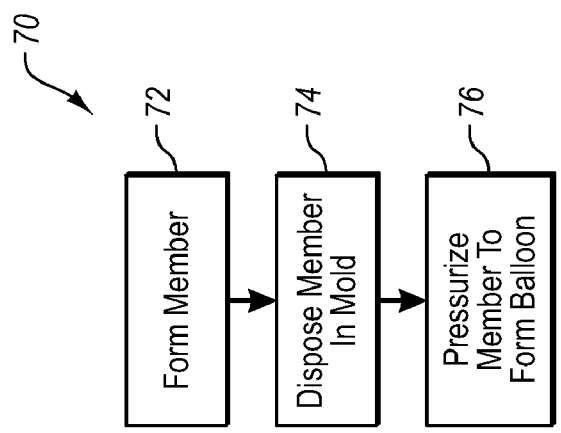

MEDICAL DEVICE BALLOON

CROSS-REFERENCE TO RELATED APPLICATIONS

This application claims the benefit of U.S. Provisional Patent Application Ser. No. 60/698,581, filed Jul. 12, 2005, the disclosure of which is incorporated herein by this reference.

BACKGROUND OF THE INVENTION

1. The Field of the Invention

The present invention relates to medical devices that can be placed in bodily conduits. More specifically, the invention relates to balloons and catheters using such balloons for administering treatments to widen constricted passages, deliver therapeutic agents, deliver endoprosthesis' or perform other medical procedures.

2. The Relevant Technology

Balloon catheters are well known for their utility in medical procedures. Typically, balloon catheters have a balloon fastened at least at one end around the exterior of a hollow catheter shaft. The hollow interior of the balloon is in fluid flow relation with the hollow interior of the shaft. Fluid under pressure can be supplied to the interior of the balloon through the shaft to expand the balloon against an obstruction.

Presently catheter balloons may be classified as compliant, semi-compliant, or non-compliant balloons. Compliance can be defined as the increase in diameter from nominal balloon pressure to rated burst pressure. Non-compliant balloons have less increase in diameter, than semi-compliant balloons, which in turn have less increase in diameter than compliant balloons.

Compliant balloons expand and stretch with increasing pressure within the balloon, and are made from such materials as polyethylene or polyolefin copolymers. Non-compliant balloons, made from such materials as polyethylene terephthalate (PET) or polyamides, remain substantially at a preselected diameter as the internal balloon pressure increases beyond that required to fully inflate the balloon.

Compliant balloon materials provide a degree of softness to the balloon which aids its passage through, e.g., blood vessels with minimal trauma. Known compliant balloon materials also can display good abrasion and puncture resistance at thicknesses typically used for medical device balloons. However, as mentioned above, they do not remain at the desired diameter with increasing pressure. Such compliant balloons also lack sufficient hoop strength to achieve high dilating forces.

A non-compliant balloon, that is one remaining at a preselected diameter regardless of increasing pressure, is often desirable. Typical non-compliant balloon materials do not exhibit the same degrees of softness and abrasion resistance as the compliant balloons.

It would be desirable, for many treatment conditions, to have a dilatation balloon exhibiting the combined characteristics of softness, abrasion and puncture resistance, hoop strength, and the ability to maintain a preselected diameter as the internal pressure within the balloon is increased. The balloon described herein was developed to address that need.

BRIEF SUMMARY OF THE INVENTION

In accordance with the present invention there is provided a balloon catheter having an expandable balloon disposed adjacent a distal end of an elongated catheter shaft. The balloon can be constructed of a novel absorbable biomaterial. The absorbable biomaterial can include tissue compatible material and/or component molecules that occur naturally in mammals. In one configuration, the biomaterial can be a material chosen from 4-hydroxybutyrate, 3-hydroxybutyrate, or a blend of 4-hydroxybutyrate or 3-hydroxybutyrate.

In another configuration, a balloon catheter is provided that includes an elongated tubular member having a proximal end and a distal end. A hub is mounted to a proximal end of the tubular member, with a biosynthetic balloon disposed adjacent the distal end of the elongated tubular member. The biosynthetic balloon can be constructed of a biosynthetic polyester or other suitable biosynthetic material and can be semi-compliant.

The above summary of some embodiments is not intended to describe each disclosed embodiment or every implementation of the present invention. The Figures, and Detailed Description which follows, more particularly exemplify these embodiments. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1A is a plan view of an exemplary embodiment of a balloon catheter in accordance with the present invention.

FIG. 1B is a cross-sectional side view of a portion of the balloon catheter of FIG. 1A.

FIG. 1C is a cross-section side view of an alternate configuration of a catheter shaft of the balloon catheter of FIG. 1A.

FIG. 2 is a flow diagram schematic representation of a manufacturing process associated with the balloon catheter of FIG. 1A.

FIG. 3 is a plan view illustrating an endoprosthesis disposed radially about a balloon in accordance with the balloon catheter of FIG. 1A.

DETAILED DESCRIPTION

Figure 4:
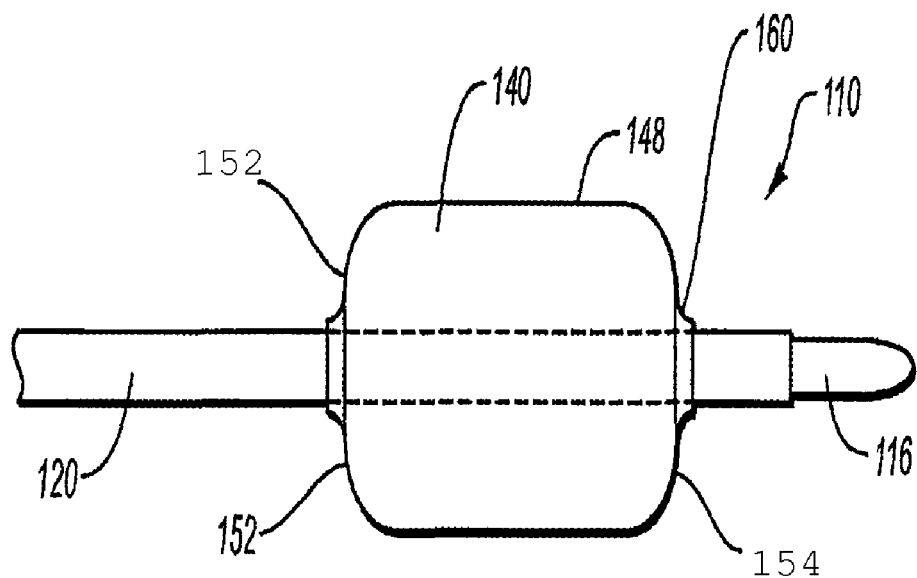
FIG. 4 is a plan view of an alternative balloon catheter illustrating an alternate mounting of the balloon to the catheter shaft.
Figure 5:
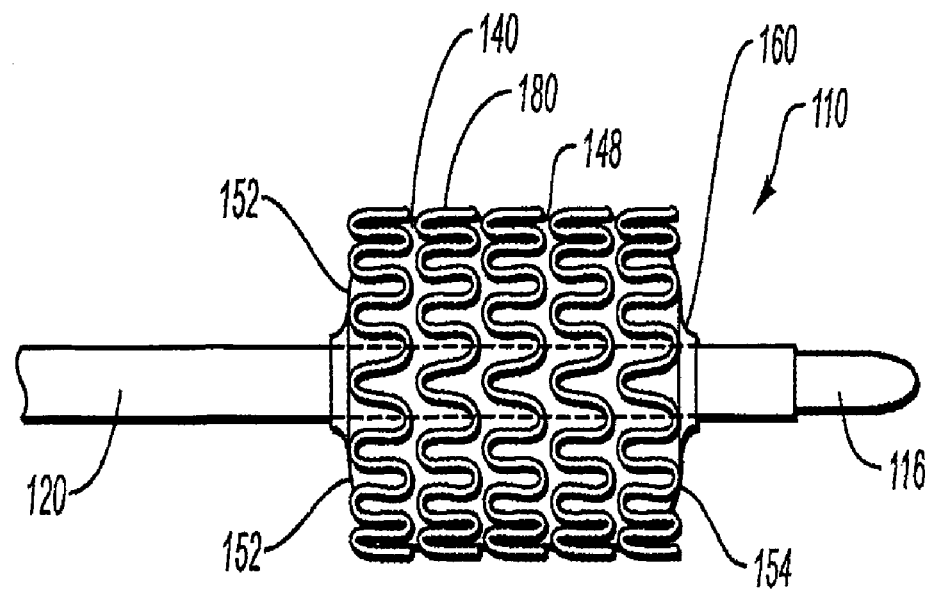
FIG. 5 is a plan view illustrating an endoprosthesis disposed radially about an expanded balloon of FIG. 4 according to the alternative affixing method.

The present invention generally relates to medical devices, such as balloon catheters usable during a medical procedure. The medical device can include an expandable balloon member which is flexible, yet exhibits desired tensile strength for application of the desired internal pressures. The balloon catheters in accordance with the present invention may be utilized in medical procedures such as administering treatments to widen constricted passages, deliver therapeutic agents or perform other medical procedures.

Although reference will be made herein to specific exemplary embodiments of one medical device, the description is illustrative of the invention and is not to be construed as limiting the invention. Various modifications to the present invention can be made to the embodiments by those skilled in the art without departing from the true spirit and scope of the invention as defined by the appended claims. It will be noted here that for a better understanding, like components are designated by like reference numerals throughout the various figures. Further, the following detailed description should be read with reference to the drawings in which similar elements in different drawings are numbered the same. The drawings, which are not necessarily to scale, depict illustrative embodiments and are not intended to limit the scope of the invention.

For purposes of illustration and not limitation, referring now to FIG. 1A, there is shown an exemplary embodiment of a balloon catheter, identified by reference numeral 10. The balloon catheter 10 can include a proximal end 12 and a distal end 14 and can be sufficiently flexible to be positioned through the tortuous anatomy of a patient's vasculature into any bodily conduit. In the illustrated configuration, the balloon catheter 10 can include an elongated tubular member or catheter shaft 20 having a proximal end 22 and a distal end 24, a hub 30 mounted to the proximal end 12 of the balloon catheter 10 and the elongated tubular member 20, and a balloon 40 mounted toward the distal end 14 of the balloon catheter 10 upon the elongated tubular member 20.

Turning first to the elongated tubular member 20, at least one inflation lumen 26 (FIG. 1B) and at least one guidewire lumen 28 (FIG. 1B) extend from the proximal end 22 toward the distal end 24. The at least one inflation lumen 26 extends from the proximal end 22 and terminates in close proximity to the balloon 40 so that the at least one inflation lumen 26 is in fluid communication with an interior chamber 42 of the balloon 40. In the illustrated configuration, a portion of the elongated tubular member 20 includes at least one port 44 that communicates with both the interior chamber 42 of the balloon 40 and the at least one inflation lumen 26. In this manner, fluid directed into the at least one inflation lumen 26 flows to and through the at least one port 44 to deploy or expand the balloon 40. Similarly, fluids can be drawn from within the interior chamber 42 of the balloon 40 through the at least one port 44 to un-deploy or deflate the balloon 40 or otherwise reduce the pressure of the fluid within the balloon 40.

The elongated tubular member 20 may be constructed of biocompatible materials or non-biocompatible materials coated with a biocompatible material. For instance, and not by way of limitation, the elongated tubular member 20 may be at least partially constructed of a material such as a synthetic material, a plastic, a composite, combinations thereof, a medical grade synthetic material or plastic, or the like. Exemplary materials may include, but are not limited to, polyurethane, polytetrafluoroethylene (PTFE) and other fluoropolymers, nylon, polyvinyl chloride (PVC), and other biocompatible materials. The elongated tubular member 20 may also be at least partially constructed of a metal material, such as, but not limited to, stainless steel, or a shape memory alloy, such as but not limited to Nitinol.

The elongated member 20 may be constructed from an extruded tubular member having one or more lumens, such as the at least one inflation lumen 26 and the at least one guidewire lumen 28. These lumens 26 and 28 can be formed during the extrusion process. Alternatively, the lumens 26 and 28 can be constructed of separate tubular members which are then positioned relative to each other to create the at least one inflation lumen 26 and the at least one guidewire lumen 28. The relative orientations and positions of the lumens 26 and 28 can be varied depending upon the particular configuration of the elongated member. For instance, in one configuration the at least one guidewire lumen 28 is within the at least one inflation lumen 26. In another configuration, the at least one guidewire lumen 28 may be disposed outside of the at least one inflation lumen 26. In still another configuration, the at least one guidewire lumen 28 extends through the balloon 40, while the at least one inflation lumen 26 terminates at or distal to a proximal end or portion of the balloon 40, while communicating with the interior chamber 42.

Although reference is made to the elongated tubular member 20 being a tubular structure, it will be appreciated, and with reference to FIG. 1C, the elongated tubular member 20 may be constructed of more than one layer of material. For example, and with exclusion to identification of the inflation lumen and the guidewire lumen for simplicity, there may be an inner tubular member 20a, a reinforcement member or layer 20b disposed about the inner tubular member 20a and an outer tubular member 20c disposed about the reinforcement member or layer 20b. The reinforcement member or layer 20b can have a lattice structure, a braided configuration, or other structure or configuration to provide strength and desired rigidity to the elongated tubular member.

Each of the inner tubular member 20a, the reinforcement member or layer 20b, and the outer tubular member 20c can be constructed of a material similar to those described herein. In addition, the reinforcement member or layer 20b, and other portions of the elongated tubular member 20 can be constructed from a shape memory material, such as a shape memory alloys ("SMA") comprised of metal alloys, shape memory plastics ("SMP") comprised of polymers, or shape memory metals ("SMM").

The main types of SMAs include: copper-zinc-aluminum; copper-aluminum-nickel; nickel-titanium ("NiTi") alloys known as Nitinol; and cobalt-chromium-nickel alloys or cobalt-chromium-nickel-molybdenum alloys known as Elgiloy. However, other types of SMAs can be used. Typically, the nitinol and Elgiloy alloys can be more expensive, but have superior mechanical characteristics in comparison with the copper-based SMAs. Examples of SMPs include biodegradable polymers, such as oligo($\epsilon$-caprolactone)diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

Returning to FIG. 1A, the hub 30 is disposed adjacent the proximal end 22 of the tubular member 20. The hub 30 can include at least one lumen to communicate with the at least one inflation lumen 26 (FIG. 1B) and the at least one guidewire lumen 28 (FIG. 1B). For instance, and illustrated by dotted lines in FIG. 1A, a lumen 32 of the hub 30 is in fluid communication with the inflation lumen 26 (FIG. 1B) of the elongated tubular member 20, while a second lumen 34 is associated with the guidewire lumen 28 (FIG. 1B) of the tubular member 20. It is contemplated that the hub 30 can have numerous different configurations to enable various medical devices to be releasable and/or sealably mounted thereto. For instance, the hub 30 can include at least one luer lock fitting or other similar structures to facilitate sealed mounting of a medical device, such as a syringe. Various other structures and configurations are possible and known to those skilled in the art in light of the teaching contained herein.

With continued reference to FIG. 1A, the balloon 40 can be disposed radially about the tubular member 20 and adjacent the distal end 24 of the tubular member 20. The balloon 40 may be constructed in a manner such that it exhibits noncompliant characteristics, compliant characteristics, or any combination thereof The balloon 40 can include a proximal portion 46, an intermediate portion 48, and a distal portion 50. Disposed between the proximal portion 46 and the intermediate portion 48 is a shoulder 52, while disposed between the intermediate portion 48 and the distal portion 50 is a shoulder 54. The proximal portion 46 and the distal portion 50 function as mounting portions to enable the balloon 40 to be mounted to the outer surface of the tubular member 20 to create the interior chamber 42 of the balloon 40. With the proximal portion 46 and the distal portion 50 mounted to the tubular member 20, the interior chamber 42 is in fluid communication with the inflation lumen 26 (FIG. 1B) of the elongated tubular member 20.

The proximal portion 46 and the distal portion 50, or a separate portion of the balloon 40, can be used to mount the balloon to the elongated tubular member 20. Mounting of the balloon 40 can be achieved through use of an adhesive, welded bond, swaging or other known attachment methods. Optionally, a band 60, such as a radiopaque marker band, may be utilized to attach the proximal portion 46 and/or the distal portion 50 of the balloon 40 to the elongated tubular member 20 or may be used in combination with the above processes. Additional radiopaque markers or marker bands may be secured to the outer surface of the elongated tubular member 20 at any position along its length, including within the interior chamber 42 of the balloon 40.

The marker bands can be constructed of materials that facilitate or provide radiopacity. These materials may include, but are not limited to, platinum, alloys of platinum, gold, or combinations thereof, metals, alloys, plastic, polymer, synthetic material, combinations thereof, or other materials that provide an appropriate radiopaque signature. Alternatively, portions of the catheter 10, including the balloon 40 and/or the elongated tubular member 20 may be coated with an appropriate radiopaque material, such as, but not limited to, barium sulphate, bismuth subcarbonate, titanium dioxide, or combinations thereof, to provide radiopacity.

The balloon 40 may be constructed of various absorbable biomaterials. One such material is biosynthetic polyester which, advantageously, is tissue compatible and is constructed of component molecules that occur naturally in mammals. The biosynthetic polyester exhibits desirable characteristics for medical device balloons. For instance, biosynthetic polyesters are very flexible; yet exhibit tensile strengths that are similar to ultrahigh molecular weight polyethylene. These characteristics provide for a balloon that can be tracked through tortuosity easily and has an acceptably high burst pressure.

Illustrative biosynthetic polyesters are available from Tepha® under the tradenames of TephaFLEX which is comprised of (4-hydroxybutyrate) and TephELAST which is comprised of (3-hydroxybutyrate). As such, the balloon of the balloon catheter can be constructed from the above-identified polyesters, combinations or blends of these polyesters, whether alone or in combination with other materials, or other bioabsorbable materials. Biosynthetic polyester materials can be constructed in a bioreactor according to the process disclosed in U.S. Pat. No. 6,495,152, the entirety of which is hereby incorporated by reference. The materials can be post processed in a number of ways including, for example and not by way of limitation, extrusion, molding, such as by injection or dipping, textile processing such as weaving or braiding, and forming. Forming processes that may be suitable are rolling and welding sheets of material or vacuum forming into tubular shapes. In addition to the above-described materials, the balloon 40 can also be constructed of poly-L-lactide-co-glycolide, poly-dL-lactide-co-glycolide, polyester amide, chitosan, polybutylene terephthalate (PBT), and polyethylene glycol (PEG), to name a few.

In accordance with the present invention, the above described materials can be formed into the balloon 40 using a balloon blowing process, identified by reference numeral 70 in FIG. 2. For instance, and not by way of limitation, the process 70 can include forming a generally tubular member of the biosynthetic polyester, as represented by block 72. This can be performed though extrusion, rolling, dip molding, or other processing techniques. Once formed, the generally tubular member can be placed or inserted within a balloon mold in a balloon forming machine, as represented by block 74. When disposed in the mold of the balloon forming machine and the mold is closed, the inner lumen of the tubular member can be pressurized and force can be applied to the ends of the tubular member to form the balloon 40, as represented by block 76. The mold can be depressurized following balloon formation and balloon 40 removed from the mold. Optionally, the mold can be heated to further conform the material to the mold during the process 70. It is further contemplated that the balloon in accordance with the present invention may be fabricated using other known techniques such as dip molding, spray coating/molding, rotational molding, wrap molding technique where a sheet of material is wrapped around a mandrel wherein the material is either blown to a final diameter or molded to a final diameter thereby fusing the wrapped material together. The fabrication techniques listed above should be considered exemplary. It is contemplated that the balloon may be manufactured through other methods and techniques not described herein without departing from the scope of the invention.

With continued reference to FIG. 1A, mounted to the distal end 24 of the elongated tubular member 20 is a tip 16. This tip 16 can form the distal end 14 of the catheter 10 and optionally be constructed of a different material than that of the tubular member 20. The tip 16 can be constructed having more flexible or pliable properties than that of the tubular member 20, thereby providing an atraumatic tip on the medical device 10. For instance, in one configuration the tip 16 can include a core that is surrounded by a flexible coil which terminates at the distal end in an atraumatic portion, such as a solder ball or other mechanism for forming an atraumatic distal end of the tip 16. In another configuration, the at least one guidewire lumen 28 passes through the tip 16 and the tip 16 has flexible or pliable properties. More generally, the atraumatic tip 16 can have a variety of other configurations so long as atraumatic tip is flexible and optionally shapeable. Furthermore, atraumatic tip 16 may be radiopaque to allow steerable positioning of the catheter 10 while allowing a physician or clinician to observe the location of tip 16 using appropriate devices, such as a fluoroscopic device or X-ray device. Tip 16, therefore, can be constructed of the radiopaque materials or coatings described herein or otherwise known to one skilled in the art in light of the teaching contained herein.

The balloon catheter 10 described herein can be used either alone or in combination with an endoprosthesis 80 that can be radially disposed about the balloon 40, as shown in FIG. 3. The endoprosthesis 80, such as a stent, may be expanded from a crimped profile to an expanded profile by inflating the balloon 40. As shown in FIG. 3, portions of the intermediate portion 48 can expand outwardly from the peripheral edge of the endoprosthesis 80. The endoprosthesis 80 may include a beneficial agent or drug disposed thereon or therein. For example, therapeutic agents, pharmaceuticals and radiation therapies may be disposed on or in or form part of the endoprosthesis 80.

Such drugs or beneficial agents can include, but are not limited to, antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors having beneficial gene, genes, siRNA, antisense compounds, oligionucleotides, cell permeation enhancers, and combinations thereof Another example of a suitable beneficial agent is described in U.S. Pat. No. 6,015,815 and U.S. Pat. No. 6,329,386 entitled "Tetrazole-containing rapamycin analogs with shortened half-lives", the entireties of which are herein incorporated by reference.

Referring now to FIG. 4, illustrated is an alternate version of the balloon catheter of the present invention. The balloon catheter 110 is similar to that of balloon catheter 10 described herein, however, a balloon 140 differs from the balloon 40 (FIG. 1A) of the balloon catheter 10 (FIG. 1A). As such, the description of balloon catheter 10 also applies to the description of balloon catheter 110, with like structures being identified with like reference numerals.

With continued reference to FIG. 4, the balloon 140 mounts to a tubular member 120. Unlike the balloon 40 (FIG. 1) where the proximal portion 46 and the distal portion 50 function as mounting portions, the balloon 140 can be mounted to the tubular member 120 by way of the shoulders 152 and 154, thus eliminating the proximal portion and distal portion described above. The shoulders 152 and 154 can be gathered and affixed to the tubular member 120 by crimping a band, such as, but not limited to, a marker band 160 upon a portion of each of the shoulders 152 and 154. Affixing of the shoulders 152 and 154 may also be achieved by crimping alone or through the use of adhesives, lasers treatment, white light, melting, combinations of any of the above, or other manners of mounting an inflation balloon to a tubular member.

Although reference is made to mounting the balloon 140 to the tubular member 120, without the balloon 140 having the proximal portion and distal portion, it will be understood that the process of mounting balloon 140 to tubular member 120 can also be practiced with mounting the balloon 40 (FIG. 1A) to the tubular member 20 (FIG. 1A). For instance, once the shoulders 52 and 54 (FIG. 1A) are used to mount the balloon 40 (FIG. 1A), the proximal portion 46 and the distal portion 50 may be cut away or otherwise removed from the balloon 40 (FIG. 1A). It will be understood that the proximal portion 46 and the distal portion 50 can be removed through various other techniques or methods. For example, the proximal portion 46 and the distal portion 50 can be removed using thermal or chemical treatments, slicing, scoring, laser cutting, water jet cutting, combinations thereof, or other techniques for separating a portion of the balloon from the reminder of the balloon.

In the illustrated configuration, the ends of the balloon 140 become rounded when in an expanded condition, forming sausage like shoulders 152 and 154 on the balloon 140. This type of feature is desirable in that it reduces the stiffness of the shoulder portion of the balloon 140, thereby increasing the flexibility and conformance of the balloon 140. Additionally, and with reference to FIG. 4, when the endoprosthesis 80 is mounted on the balloon 140, the rounded shoulders 152 of the balloon 140 do not project beyond the endoprosthesis 80, such that the endoprosthesis 80 rests substantially upon an intermediate portion 148 of the balloon 140. This reduces the overall dimensions of the balloon 140 of the balloon catheter 110 and enables the balloon catheter 110 to be more easily steered through the tortuous anatomy of the patient. In addition, contact between a portion of the balloon and the vessel wall during balloon expansion, and stent deployment is eliminated, thereby eliminating or substantially decreasing the possibility of vessel dissection and/or irritation resulting from vessel wall/balloon contact.

Although the present invention has been shown and described with reference to specific materials and processes this should not be considered limiting in any manner, it is contemplated that one of ordinary skill in the art may modify the present invention without departing from the scope of the invention. As such, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A balloon catheter, comprising
an elongated shaft having a proximal end and a distal end; and
a bioabsorbable balloon disposed adjacent the distal end, wherein the balloon is made from a semi-compliant membrane affixed to the shaft so as to be able to inflate and deflate, and the inflatable membrane itself is constructed of a blend of biosynthetic polyesters, the blend comprising a first polyester formed from one or more monomers, one of which is 4-hydroxybutyrate and the blend also comprising a second polyester formed from one or more monomers, one of which is 3-hydroxybutyrate.

2. The balloon catheter according to claim 1, further comprising an inflation lumen, the inflation lumen in fluid communication with an interior of the balloon and the proximal end of the shaft, and further comprising a guidewire lumen substantially disposed outside the inflation lumen.

3. The balloon catheter according to claim 2, further comprising a hub associated with the proximal end of the shaft, and including at least one lumen associated with the inflation lumen.

4. The balloon catheter according to claim 1, wherein the semi-compliant membrane is constructed of a tissue compatible material.

5. The balloon catheter according to claim 1, wherein the semi-compliant membrane is constructed of component molecules that occur naturally in mammals.

6. The balloon catheter according to claim 1, wherein the blend is a blend of poly(4-hydroxybutyrate) and poly(3-hydroxybutyrate).

* * * * *